US012014809B2

United States Patent
Oliveira Santos et al.

(10) Patent No.: US 12,014,809 B2
(45) Date of Patent: Jun. 18, 2024

(54) CALIBRATION OF ORIENTATIONS OF A GYROSCOPE OF A MOTION TRACKING SYSTEM

(71) Applicant: SWORD HEALTH S.A., Oporto (PT)

(72) Inventors: Pedro Henrique Oliveira Santos, Oporto (PT); Luís Ungaro Pinto Coelho, Oporto (PT); Marta Maria Ramalho Ferreira, Oporto (PT); Ana Clara Ferreira Matos, Oporto (PT); Virgílio António Ferro Bento, Oporto (PT)

(73) Assignee: SWORD HEALTH, S.A., Oporto (PT)

(*) Notice: Subject to any disclaimer, the term of this patent is extended or adjusted under 35 U.S.C. 154(b) by 305 days.

(21) Appl. No.: 17/604,671

(22) PCT Filed: Apr. 27, 2020

(86) PCT No.: PCT/EP2020/061653
§ 371 (c)(1),
(2) Date: Oct. 18, 2021

(87) PCT Pub. No.: WO2020/221704
PCT Pub. Date: Nov. 5, 2020

(65) Prior Publication Data
US 2022/0215925 A1 Jul. 7, 2022

(30) Foreign Application Priority Data

Apr. 30, 2019 (EP) .................... 19398005

(51) Int. Cl.
*G16H 20/30* (2018.01)
*A61B 5/00* (2006.01)

(52) U.S. Cl.
CPC ........... *G16H 20/30* (2018.01); *A61B 5/6823* (2013.01); *A61B 5/6824* (2013.01);
(Continued)

(58) Field of Classification Search
CPC ...... G16H 20/30; G16H 30/20; A61B 5/6823; A61B 5/6824; A61B 2560/0223;
(Continued)

(56) References Cited

U.S. PATENT DOCUMENTS

2017/0189752 A1\* 7/2017 Mohrman .......... G09B 19/0038
2018/0140229 A1 5/2018 Kesaniemi

FOREIGN PATENT DOCUMENTS

| EP | 1970005 | 9/2008 |
| EP | 1970005 A1 | 9/2008 |
| WO | 2020221704 | 11/2020 |
| WO | WO-2020221704 A1 | 11/2020 |

OTHER PUBLICATIONS

International Search Report dated Sep. 3, 2020 re: Application No. PCT/EP2020/061653, pp. 1-4, citing: US 2017/189752 A1, EP 1 970 005 A1, Zhao et al., "Towards a Data-Driven . . .", Seel et al. "IMU-Based Joint Angle . . . ", US 2018/140229 A1.
(Continued)

*Primary Examiner* — Eric S. McCall
*Assistant Examiner* — Timothy P Graves
(74) *Attorney, Agent, or Firm* — SCHWEGMAN LUNDBERG & WOESSNER, P.A.

(57) ABSTRACT

A method for adjusting operation of a motion tracking system at least including first and second sensors and a computing device, each of the sensors at least having a gyroscope. The method includes the following steps: arranging the first sensor on an upper arm of a person, and the second sensor on their chest; measuring orientations each of the first and second sensors while the person performs a predetermined movement. The movement includes the person moving a torso with respect to their hip while keeping the upper arm parallel to the torso and not rotating the upper arm. The method further includes digitally processing, the computing device, the orientations measured so as to digi-
(Continued)

tally compute an orientation difference between the orientations measured by the first sensor and by the second sensor; and adjusting, the computing device, the operation of the motion tracking system based on the orientation difference computed.

20 Claims, 4 Drawing Sheets

(52) U.S. Cl.
CPC ............... *A61B 2560/0223* (2013.01); *A61B 2562/0219* (2013.01); *A61B 2562/0223* (2013.01)

(58) Field of Classification Search
CPC .... A61B 2562/0219; A61B 2562/0223; A61B 5/11; G01C 25/005
See application file for complete search history.

(56) References Cited

OTHER PUBLICATIONS

Junqi Zhao, et al., "Towards a Data-Driven Approach to Injury Prevention in Construction", International Conference On Computer Analysis of Images and Patterns, Caip Computer Analysis of Images and Patterns, May 19, 2018, pp. 385-411, XP047474644, [Lecture Notes in Computer Science].

Thomas Seel, et al., "IMU-Based Joint Angle Measurement for Gait Analysis", Sensors, Apr. 16, 2014, vol. 14, No. 4, pp. 6891-6909, XP055356810, www.mdpi.com/journal/sensors.

Written Opinion dated Sep. 3, 2020 re: Application No. PCT/EP2020/ 061653, pp. 1-5, citing: US 2017/189752 A1, EP 1 970 005 A1, Zhao et al., "Towards a Data-Driven . . . ", Seel et al. "IMU-Based Joint Angle . . . ", US 2018/140229 A1.

"International Application Serial No. PCT EP2020 061653, International Search Report mailed Sep. 3, 2020", 4 pgs.

"International Application Serial No. PCT EP2020 061653, Written Opinion mailed Sep. 3, 2020", 5 pgs.

"International Application Serial No. PCT EP2020 061653, International Preliminary Report on Patentability mailed Nov. 11, 2021", 7 pgs.

"European Application Serial No. 19398005.9, Extended European Search Report mailed Nov. 15, 2019", 6 pgs.

"European Application Serial No. 20720106.2, Extended European Search Report mailed Nov. 30, 2021", 5 pgs.

Seel, Thomas, "IMU-Based Joint Angle Measurement for Gait Analysis", Sensors, vol. 14, No. 4, (Apr. 16, 2014), 6891-6909.

Zhao, Junqi, "Towards a Data-Driven Approach to Injury Prevention in Construction", International Conference on Computer Analysis of Images and Patterns. CAIP 2017: Computer Analysis of Images and Patterns; [Lecture Notes in Computer Science; Lect. Notes Computer], (May 19, 2018), 385-411.

\* cited by examiner

CALIBRATION OF ORIENTATIONS OF A GYROSCOPE OF A MOTION TRACKING SYSTEM

TECHNICAL FIELD

The present invention relates to the field of motion tracking of a person. More specifically, the present invention relates to the determination of the motion of the person tracked when using wearable motion tracking sensors.

STATE OF THE ART

Motion tracking or motion capture is becoming a key technique in different applications in which the movement of a target such as a person is an important part of a process of the applications.

Different types of sensors are suitable for tracking or capturing the movement of a target. Optical sensors record images or video of the target and a computing device digitally processes the images or video so as to provide a movement sequence of the target. Other suitable sensors are wearable sensors, which are arranged on the target and measure different magnitudes that are indicative of the movement of the target.

Wearable sensors may include one or more sensing devices such as gyroscopes, accelerometers, magnetometers, etc. By processing the measurements of one or several of these sensing devices, the movement sequence of the target may be determined, at least the movement sequence of the tracked parts of the target.

Since each sensor operates independently, an essential aspect of such motion tracking is the calibration of the wearable sensors. Consequently, if the sensors are not calibrated, the complete processing of the measurements of the sensors by the computing device provides a movement sequence of the tracked parts that does not match the movement performed by the person.

The sensors are, thus, subjected to some kind of calibration every once in a while. The type of calibration and the frequency with which the same has to be performed at least depends on the sensors used (each type of sensing device has a different behavior and, hence, the error it cumulates over the time is different) and the accurateness of the measurements required by the application.

Usually, the fewer sensing devices a sensor has, the more necessary a calibration is required since there are few (or none) other sensing devices that can compensate for the errors in the measurements of the sensing devices within the sensor. This is the case, for instance, when the sensors provide orientations based on the measurements of gyroscopes, being these complemented or not by measurements of accelerometers.

There is an interest in providing a method for determining the placement of sensors with gyroscopes and/or adjusting the way in which the motion tracking system comprising said sensors behaves. There is also an interest that said method has a reduced complexity so that the person using the motion tracking system adjusts the placement of one sensor with respect to the placement of another sensor in order to provide an accurate movement sequence.

DESCRIPTION OF THE INVENTION

A first aspect of the invention relates to a method for adjusting operation of a motion tracking system at least comprising first and second sensors and a computing device, each of the first and second sensors at least comprising a gyroscope, the method comprising: arranging the first sensor on an upper arm of a person, and the second sensor on a chest of the person; measuring orientations each of the first and second sensors while the person performs a predetermined movement, the predetermined movement comprising the person moving a torso thereof with respect to a hip of the person while keeping the upper arm parallel to the torso and not rotating the upper arm; digitally processing, the computing device, the orientations measured so as to digitally compute an orientation difference between the orientations measured by the first sensor and the orientations measured by the second sensor; and adjusting, the computing device, the operation of the motion tracking system based on the orientation difference computed.

The predetermined movement and the arrangement of the first and second sensors (on the upper arm and the chest, respectively) are such that it is possible to determine the placement of the first sensor with respect to the placement of the second sensor.

When a predetermined sensor arrangement stored in the computing device is such that the sensors are to be arranged on the person with a same orientation while both the upper arm and the chest have a same orientation, the orientations measured by the first sensor and the orientation measured by the second sensor should be the same to an extent, but not exactly the same due to errors introduced by the sensors themselves (the electronics of the sensors are not perfect), imperfect reproduction of the movement, imperfect sensor arrangement on the person, etc. The computing device computes the difference between the measured orientations. This, in turn, makes possible to adjust the motion tracking system so as to take into account this difference either during the motion tracking procedure or in the subsequent use, by an application, of the motion sequence provided by the motion tracking system, or even pause or stop the motion tracking procedure until the difference computed is reduced. The latter may be attained, for instance, by rearranging the first sensor on the upper arm of the person.

The method of the present disclosure, however, is not limited to predetermined sensor arrangements in which both the first and second sensors are to be arranged on the person with a same orientation while both the upper arm and the chest have a same orientation. The orientation difference between the first and second sensors depending on the predetermined sensor arrangement is taken into account when the computing device adjusts the operation of the motion tracking system based on the orientation difference computed.

Either one of the first and second sensors, and particularly the measurements thereof, may be used as reference for the measurements of the other one of the first and second sensors. Notwithstanding, it is preferable to use as reference the sensor arranged on the chest of the person, i.e. the second sensor, because arranging a sensor on the chest is less prone to inaccurate attachment by the person owing to the shape of the chest (compared with the shape of the upper arm).

The predetermined movement involves the movement of both the torso and the upper arm in such a way that the upper arm undergoes the same motion of the torso. The torso is moved with respect to the hip so as to tilt the posture of the person. During the movement, the upper arm is not rotated with respect to a shoulder of the person connected to the upper arm so that the orientation measurements of the first sensor are not altered due to such rotation. As the upper arm is moved following the torso, both the torso and the upper arm undergo a same (or almost the same) motion, therefore the orientation measurements of both the first sensor and the second sensor are used for determining the placement of one sensor with respect to the placement of the other sensor.

The initial and final orientations are, thus, used for both determining said placement and adjusting the operation of the system; differences between the determined placement of the sensor and the expected placement of the sensor are taken into account for the operation of the system. The operation of the motion tracking systems may be adjusted in several ways based on the orientation difference computed.

It is to be noted that, in some cases, the orientation difference is not due to an incorrect arrangement of the sensors on the person but due to the error in the measurements of the sensors themselves. The arrangement is considered incorrect if the sensors are not attached at particular positions or areas of the body members as registered in the computing device in the form of a predetermined sensor arrangement; the computing device assumes that the sensors are placed on the person according to the predetermined sensor arrangement stored in a memory of the computing device and, thus, provides a movement sequence under such assumption.

In some embodiments, the step of adjusting the operation of the motion tracking system comprises digitally modifying orientations measured by the first sensor or the second sensor.

As the orientation difference computed is indicative of the differences of one sensor with respect to the other sensor (in terms of the orientations being measured by the two sensors when the respective body members have a same orientation), instead of rearranging one or both sensors the computing device is capable of virtually calibrating the placement of the sensors. This virtual calibration involves the digital adjustment of the orientations measured by the first sensor or the second sensor so as to compensate for the orientation difference. Accordingly, the computing device digitally adds or subtracts an angle to previous and/or subsequent orientation measurements so that the motion capture procedure is not affected by the orientation difference; this angle addition or subtraction may be attained by applying a quaternion to the orientation measurements, as it is known in the art.

In some embodiments, the step of adjusting the operation of the motion tracking system comprises digitally adjusting a physical exercise evaluation procedure.

The computing device changes the way in which the physical exercise evaluation is to be processed based on the orientation difference computed. The computing device may adjust the physical exercise evaluation procedure in which a number of constraints defining the physical exercise are established in the algorithms for evaluating the physical exercises. The computing device may deactivate one or more of these constraints in the algorithms so that the possibly erroneous tracked parts of the physical exercise (that may result from the orientation difference) are not taken into account in such evaluation procedures.

Physical exercise evaluation procedures and, thus, algorithms for such procedures may base the physical exercise evaluation on the fulfillment of different constraints, for example two, three, four or even more constraints, each of which defines a limitation of the physical exercise, e.g. which angles, speeds, accelerations, etc. that have to be reproduced or that cannot be exceeded during the reproduction of the physical exercise. For instance, a physical exercise evaluation procedure that may be digitally adjusted is that described in commonly owned patent document EP18398006, which is hereby incorporated by reference in its entirety. This procedure determines whether a tracked target is correctly reproducing a movement defined by one or more predetermined constraints. The computing device removes or disregards predetermined constraints defining the movement to be performed, particularly second, third, and/or further predetermined constraints, in accordance with the orientation difference computed. In this way, the computing device determines whether the movement (as determined from the sensor measurements) of the tracked target is correctly reproduced based on a less demanding movement due to the reduction in predetermined constraints that have to be met. When the tracked target is a user, such adjustment of the physical exercise evaluation procedure usually results in fewer erroneous determinations of incorrect reproduction of movement by the user.

In some of these embodiments, digitally adjusting the physical exercise evaluation procedure comprises digitally adjusting an algorithm with which the motion tracking system digitally determines whether the person tracked with the first and second sensors performs a physical exercise. The algorithm is digitally adjusted by the computing device based on the orientation difference computed.

In some embodiments, the step of adjusting the operation of the motion tracking system comprises providing at least one user perceptible signal indicative of an incorrect placement of the first sensor on the upper arm and/or at least one user perceptible signal indicative of an instruction to rearrange the first sensor on the upper arm.

The computing device commands the provision of one or more user perceptible signals (e.g. visual indications, audible indications, tactile indications such as a vibration) to means for providing such user perceptible signal, e.g. a screen of the motion tracking system, loudspeakers of the motion tracking system, vibrators in the sensors themselves, etc. in order to indicate that the first sensor has been placed on the upper arm incorrectly based on a predetermined sensor arrangement stored in a memory of the computing device, in which case the motion tracking procedure is preferably stopped.

Additionally or alternatively, the computing device commands the provision of one or more user perceptible signals to the means to indicate an instruction whereby the first sensor should be rearranged on the upper arm, in which case the motion tracking procedure is preferably paused until the first sensor is correctly placed on the upper arm based on said predetermined sensor arrangement.

The computing device transmits a signal to either the means or a device controlling the means so that the one or more user perceptible signals are provided.

In some embodiments, the step of digitally processing the orientations measured comprises digitally computing the following: an angular displacement of each of the first and second sensors between a first position in which the person is standing still and a second position in which the person has performed the predetermined movement; axes of rotation of each of the first and second sensors relative to local coordinates of each of the first and second sensors, respectively, based on the respective angular displacements; and the orientation difference by digitally computing an angle between the axes of rotation of the first sensor and the axes of rotation of the second sensor.

The computing device uses the measurements of both the first and second sensors made in both the first and second positions so as to compute an angular displacement for each of the sensors, thereby obtaining a first angular displacement corresponding to the first sensor and a second angular displacement corresponding to the second sensor. The computing device then computes first axes of rotation from the first angular displacement and second axes of rotation from the second angular displacement; the axes of rotation are computed with respect to the local coordinates of the respective sensor. Then, the computing device computes the angle between the first axes of rotation and the second axes of rotation, which is indicative of the orientation difference.

In some embodiments, the computing device digitally processes the orientations measured so as to digitally compute the orientation difference irrespective of a direction in which the person has performed the predetermined movement.

The method and the motion tracking system do not necessarily require that the person performs the predetermined movement such that both the torso and the upper arm are moved in a particular direction with respect to the hip. The computing device processes the orientation measurements provided by the first and second sensors so as to determine in which direction the predetermined movement has been performed. Said determination may be made by comparing the different orientation measurements of each sensor; by processing the evolution of the different orientation measurements the computing device determines the predetermined movement performed.

In some examples, the computing device determines that the person has performed the predetermined movement when both the orientation measurements of any one or both of the first and second sensors have exceeded a predetermined threshold set in the computing device and previous orientation measurements thereof were not exceeding the predetermined threshold. To this end, the computing device processes all the orientation measurements it receives from any one or both of the first and second sensors and checks whether the most recent orientation measurement exceeds the predetermined threshold. As soon as an orientation measurement exceeds the predetermined threshold, the computing device preferably disregards subsequent orientation measurements and proceeds to digitally compute the orientation difference between the orientation measurements corresponding to the end of the predetermined movement and the orientation measurements corresponding to the position in which the person was standing still.

In some other examples, the computing device processes all the orientation measurements it receives from any one or both of the first and second sensors and establishes that the predetermined movement has ended once the orientation measurements have reached a maximum angular displacement. In these cases, the person can extend the movement of the predetermined movement as much as she/he desires, and the computing device digitally computes the orientation difference based on both the orientation measurements with maximum angular displacement and the orientation measurements in which the person was standing still. The maximum angular displacement is established, for example, by comparing a number of consecutive orientation measurements from any one or both of the first and second sensors and determining whether the most recent orientation measurements have an angular displacement that is less than the angular displacement of a previous orientation measurement (it is assumed that when this occurs, the person is performing a movement so as to reach an upright position after having performed the predetermined movement).

The two types of examples are possible in embodiments in which the person performs the predetermined movement in a particular direction as registered in the computing device, and in embodiments in which the person performs the predetermined movement in any direction of her/his choice.

In some embodiments, the method further comprises calibrating the second sensor prior to the step of measuring the orientations while the person performs the predetermined movement. In these embodiments, the second sensor preferably further comprises an accelerometer.

The sensor arranged on the chest is calibrated using the measurements of the gyroscope, and preferably also those of the accelerometer, so that the orientation measurements provided by the sensor correspond (or substantially correspond) to the orientation of the chest. The calibration is performed with a calibration procedure known in the art of sensor calibration.

The calibration of the sensor on the chest is preferable over the calibration of the sensor on the upper arm for the reasons set out above.

In some of these embodiments, the second sensor is calibrated prior to the step of arranging the second sensor on the chest of the person.

In some other embodiments, the second sensor is calibrated such that orientation measurements thereof are digitally modified once the second sensor has been arranged on the chest. In these embodiments, the second sensor further comprises the accelerometer.

In some embodiments, each of the first and second sensors further comprises a magnetometer, and in the step of measuring the orientations while the person performs the predetermined movement each of the first and second sensors does not process measurements of the magnetometers in respective sensor fusion algorithms thereof.

In many occasions, sensors of motion tracking systems also include magnetometers as one of the sensing devices thereof in addition to gyroscopes and accelerometers. Magnetometers are convenient for providing heading measurements and are, thus, useful for tracking the movement of a target such as a person, however magnetometers are prone to magnetic disturbances that may considerably affect the measurements thereof.

In order to avoid the effect of said possible magnetically disturbed measurements, the measurements of the magnetometers are disregarded in the sensor fusion algorithms of each of the first and second sensors. Accordingly, only the measurements of the gyroscope and, in some cases, also the measurements of accelerometers of the first and/or the second sensors are taken into account in the sensor fusion algorithms in order to measure the orientations while the person preforms the predetermined movement.

As it is known in the art, the sensor fusion algorithms combine measurements of different sensing devices so as to provide processed measurements that may remove some errors present in the raw measurements; many different algorithms exist in the prior art. Other than not processing the measurements of the magnetometers, the way in which the sensor fusion algorithms process measurements is not within the scope of the present disclosure.

In some embodiments, the predetermined movement further comprises having the upper arm pressed against a side of the torso of the person.

By having the upper arm pressed against the side of the torso of the person, the upper arm is less prone to rotations with respect to the shoulder connecting the upper arm with the torso; hence, the upper arm follows the motion of the torso during the movement without rotating with respect to the shoulder.

A second aspect of the invention relates to a motion tracking system comprising: first and second sensors, each sensor at least comprising a gyroscope; and a computing device comprising at least one processor and at least one memory, the at least one processor being configured, together with the at least one memory, to: digitally process orientations measured by the first and second sensors while a person having the first and second sensors arranged on an upper arm and a chest thereof, respectively, performs a predetermined movement, the orientations being processed so as to digitally compute an orientation difference between the orientations measured by the first sensor and the orientations measured by the second sensor; and adjust operation of the motion tracking system based on the orientation difference computed.

The motion tracking system is capable of adjusting the operation thereof so that, in the event that the first and second sensors provide differing orientation measurements when they are expected to provide similar orientation measurements (due to both the performance of the predetermined movement by the person and the predetermined sensor arrangement), the motion tracking procedure can compensate for or take into account the differences in orientations measurements of the sensors.

The system is configured to compute the orientation difference between the measurements of the sensors in accordance with the characteristics of a predetermined movement, thereby determining the placement of one sensor with respect to the placement of the other (e.g. the placement of the sensor on the upper arm with respect to the placement of the sensor on the chest). As each sensor provides measurements irrespective of the other sensors, in order to provide a movement sequence that is in line with the movement of the person the measurements need to be related in some way, for example by using a common reference. Accordingly, the computing device refers the orientation measurements of one sensor to the orientation measurements of the other sensor and derives one or more instructions for adjusting the operation of the motion tracking system based on the orientation difference computed.

As the predetermined movement involves the movement of the torso relative to the hip thereof and the same motion by the upper arm (that is to say, the upper arm moves in the same or substantially the same manner as the torso, without being subject to a rotation with respect to a shoulder connecting the upper arm with the torso), the first sensor (i.e. arranged on the upper arm) and the second sensor (i.e. arranged on the chest) should provide orientation measurements that are similar when the sensors have been arranged with a same (or substantially same) orientation or that differ by an angle when the sensors have been arranged with a differing orientation (when the upper arm and the chest have a similar orientation). Differences between the orientation measurements as computed by the computing device can be indicative of the error in the measurements of one of the sensors with respect to the other, due to for example: one of the sensors not being attached to the body member of the person according to the predetermined sensor arrangement registered in the computing device, one of the sensors not being calibrated and having an error component in the measurements thereof, etc.

In some embodiments, the at least one processor is configured to adjust the operation of the motion tracking system by digitally modifying orientations measured by the first sensor or the second sensor.

In some embodiments, the at least one processor is configured to adjust the operation of the motion tracking system by digitally adjusting a physical exercise evaluation procedure.

In some of these embodiments, the at least one processor is configured to digitally adjust the physical exercise evaluation procedure by digitally adjusting an algorithm with which the motion tracking system digitally determines whether the person tracked with the first and second sensors performs a physical exercise.

In some embodiments, the at least one processor is configured to adjust the operation of the motion tracking system by commanding means for providing user perceptible signals to provide at least one user perceptible signal indicative of an incorrect placement of the first sensor on the upper arm and/or at least one user perceptible signal indicative of an instruction to rearrange the first sensor on the upper arm.

In some embodiments, the at least one processor is configured to digitally process the orientations measured by digitally computing the following: an angular displacement of each of the first and second sensors between a first position in which the person is standing still and a second position in which the person has performed the predetermined movement; axes of rotation of each of the first and second sensors relative to local coordinates of each of the first and second sensors, respectively, based on the respective angular displacements; and the orientation difference by digitally computing an angle between the axes of rotation of the first sensor and the axes of rotation of the second sensor.

In some embodiments, the at least one processor is configured to digitally process the orientations measured so as to digitally compute the orientation difference irrespective of a direction in which the person has performed the predetermined movement.

In some embodiments, the at least one processor is further configured to calibrate the second sensor and/or command the second sensor to start a calibration procedure. In these embodiments, the second sensor preferably further comprises an accelerometer.

In some of these embodiments, the at least one processor is configured to calibrate the second sensor such that orientation measurements thereof are digitally modified.

In some embodiments, each of the first and second sensors further comprises a magnetometer, and each of the first and second sensors is configured to not process measurements of the magnetometers in respective sensor fusion algorithms thereof at least when measuring the orientations while the person performs the predetermined movement.

In some embodiments, the method further comprises presenting means for presenting a representation of the predetermined movement, the presenting means comprising a screen and/or audio output means.

A third aspect of the invention relates to a computer program product that has instructions which, when executed by a computing device, cause the computing device to perform the steps of: digitally processing orientations measured by first and second sensors of a motion tracking system while a person having the first and second sensors arranged on an upper arm and a chest thereof, respectively, performs a predetermined movement, the orientations being processed so as to digitally compute an orientation difference between the orientations measured by the first sensor and the orientations measured by the second sensor, the first and second sensors each comprising a gyroscope; and adjusting operation of the motion tracking system based on the orientation difference computed.

In some embodiments, the instructions cause the computing device to adjust the operation of the motion tracking system by digitally modifying orientations measured by the first sensor or the second sensor.

In some embodiments, the instructions cause the computing device to adjust the operation of the motion tracking system by digitally adjusting a physical exercise evaluation procedure.

In some of these embodiments, the instructions cause the computing device to digitally adjust the physical exercise evaluation procedure by digitally adjusting an algorithm with which the motion tracking system digitally determines whether the person tracked with the first and second sensors performs a physical exercise.

In some embodiments, the instructions cause the computing device to adjust the operation of the motion tracking system by commanding means for providing user perceptible signals to provide at least one user perceptible signal indicative of an incorrect placement of the first sensor on the upper arm and/or at least one user perceptible signal indicative of an instruction to rearrange the first sensor on the upper arm.

In some embodiments, the instructions cause the computing device to digitally process the orientations measured by digitally computing the following: an angular displacement of each of the first and second sensors between a first position in which the person is standing still and a second position in which the person has performed the predetermined movement; axes of rotation of each of the first and second sensors relative to local coordinates of each of the first and second sensors, respectively, based on the respective angular displacements; and the orientation difference by digitally computing an angle between the axes of rotation of the first sensor and the axes of rotation of the second sensor.

In some embodiments, the instructions cause the computing device to digitally process the orientations measured so as to digitally compute the orientation difference irrespective of a direction in which the person has performed the predetermined movement.

In some embodiments, the instructions cause the computing device to calibrate the second sensor and/or command the second sensor to start a calibration procedure. In some of these embodiments, the instructions cause the computing device to calibrate the second sensor such that orientation measurements thereof are digitally modified. In these embodiments, the second sensor preferably further comprises an accelerometer.

In some embodiments, the instructions cause the computing device to command each of the first and second sensors not to process measurements of the magnetometers in respective sensor fusion algorithms thereof at least when measuring the orientations while the person performs the predetermined movement.

A fourth aspect of the invention relates to a data stream which is representative of a computer program product according to the third aspect of the invention.

Similar advantages as those described with reference to the first aspect of the invention may also be applicable to the second, third and fourth aspects of the invention.

BRIEF DESCRIPTION OF THE DRAWINGS

To complete the description and in order to provide for a better understanding of the invention, a set of drawings is provided. Said drawings form an integral part of the description and illustrate embodiments of the invention, which should not be interpreted as restricting the scope of the invention, but just as examples of how the invention can be carried out. The drawings comprise the following figures.

DESCRIPTION OF WAYS OF CARRYING OUT THE INVENTION

Figure 1:
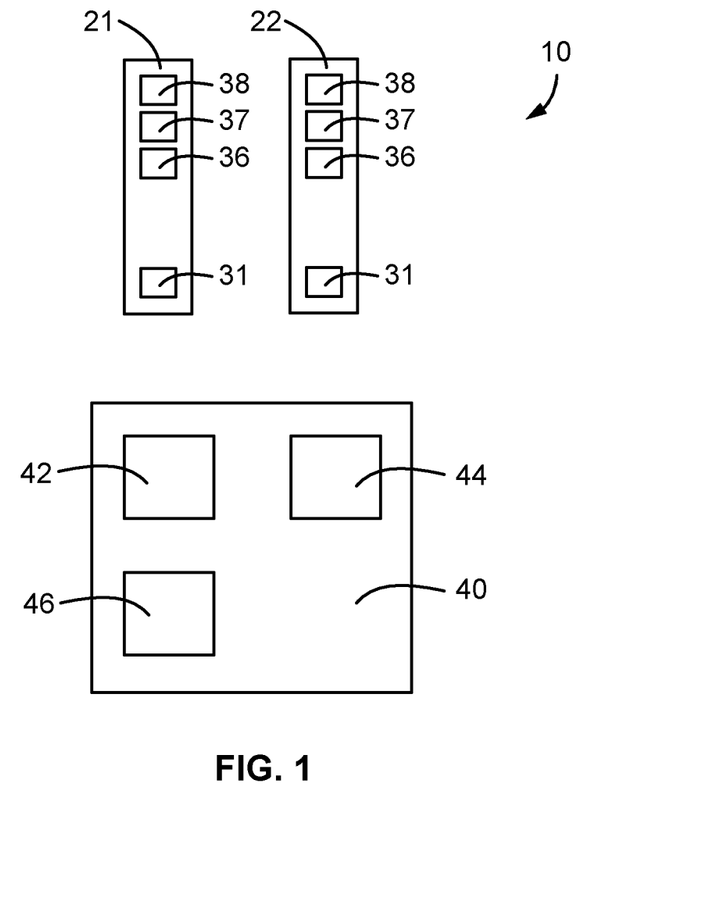
FIG. 1 diagrammatically shows a motion tracking system in accordance with an embodiment.

FIG. 1 diagrammatically shows a motion tracking system 10 in accordance with an embodiment. The motion tracking system 10 includes a plurality of sensors with first and second sensors 21, 22, and a computing device 40.

The sensors 21, 22 at least include a gyroscope 31. The sensors 21, 22 also include at least one processor 36 and at least one memory 37. In preferred embodiments such as the one of FIG. 1, the sensors 21, 22 further include a first communications module 38 for transmitting and receiving data that enables the sensors 21, 22 to transmit (through a wired or wireless communications technology and protocol known by a skilled person, for instance but without limitation, Bluetooth communications, cellular network communications such as GSM, UMTS or LTE, wireless LAN communications, etc.) measurements of the sensing device 31 to the computing device 40. The same first communications modules 38 enable the sensors 21, 22 to receive data from the computing device 40. In less preferred embodiments, the sensors 21, 22 are not provided with the first communications module 38; in these embodiments, data can be extracted from the sensors 21, 22 and/or provided to the sensors 21, 22 by means of a computer readable storage medium.

The computing device 40 includes at least one processor 42 and at least one memory 44. Preferably, the computing device 40 further includes a second communications module 46 for transmitting and receiving data. When the computing device 40 is not provided with the second communications module 46, data can be extracted therefrom and/or introduced therein by means of a computer readable storage medium.

In some embodiments, the first sensor 21 and/or the second sensor 22 further comprise an accelerometer. Also, in some embodiments, the first sensor 21 and/or the second sensor 22 further comprise a magnetometer. Accelerometers and magnetometers may assist in the measurement of orientations and/or calibration of the placement of the sensors.

In some embodiments, the plurality of sensors of the motion tracking system 10 comprise further sensors in addition to the first and second sensors 21, 22.

Figure 2A:
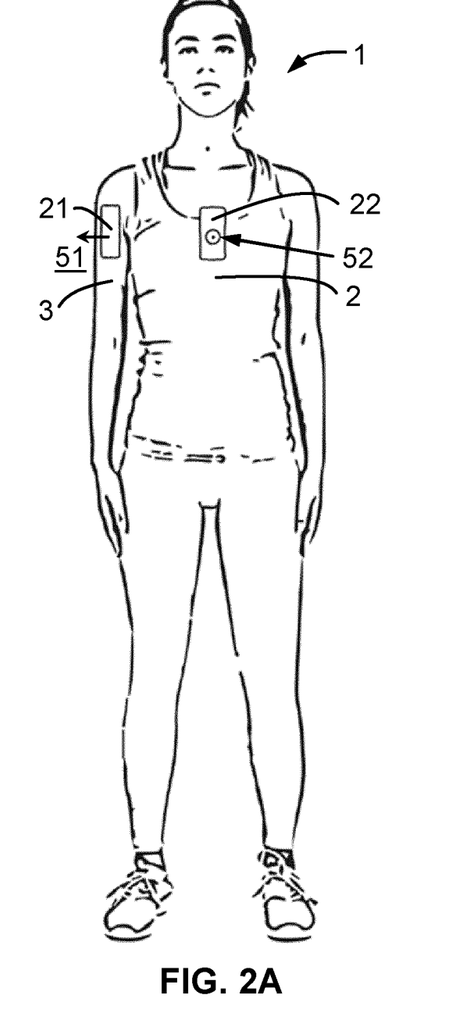
FIGS. 2A and 2B show a person standing still with sensors of a motion tracking systems attached thereon.
Figure 2B:
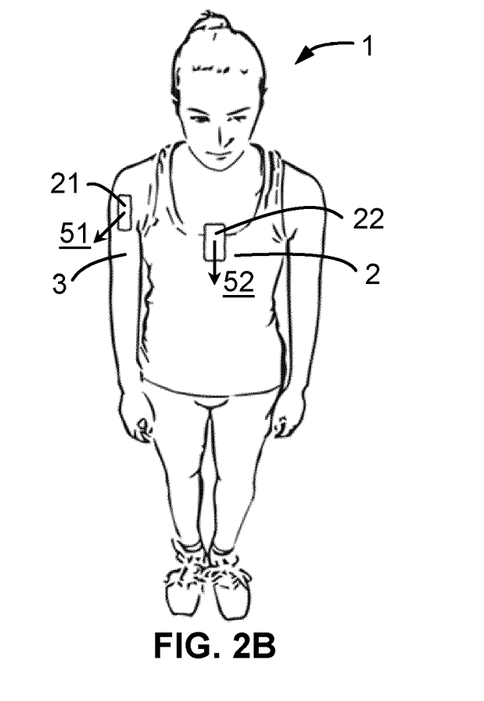

FIGS. 2A and 2B show, from two different perspectives, a person 1 standing still with sensors 21, 22 of a motion tracking system attached thereon.

The person 1 has attached on an upper arm 3 (of the right arm of the person 1) thereof a first sensor 21 (such as the first sensor 21 of FIG. 1); also, the person 1 has attached on a chest 2 thereof a second sensor 22 (such as the second sensor 22 of FIG. 1). A computing device (such as the computing device 40 of FIG. 1) has stored in a memory thereof a predetermined sensor arrangement in which it is defined that the first sensor 21 is to be placed on the upper arm 3 of the right arm (and on which part thereof and/or with what orientation), and the second sensor 22 is to be placed on the chest 2 (and on which part thereof and/or with what orientation).

For illustrative purposes only, a first orientation measurement 51 of the first sensor 21 is represented by means of an arrow, and a second orientation measurement 52 of the second sensor 22 is also represented by means of an arrow. In FIG. 2A the arrow of the second orientation measurement 52 arrow is completely front facing, i.e. coming out from the page, as it can be better appreciated in FIG. 2B.

It can be observed that even though the posture of the person 1 is completely upright with the arms being parallel to the torso of the person 1, and the first and second sensors 21, 22 have been arranged with a similar orientation in this embodiment, the first and second orientation measurements 51, 52 differ considerably. If a motion tracking procedure were to be carried out without taking into account that the orientation measurements 51, 52 differ as shown, the motion sequence resulting from the motion tracking procedure would not correspond to the movements involving the right upper arm 3 and the torso that the person 1 actually performed.

Figure 3:
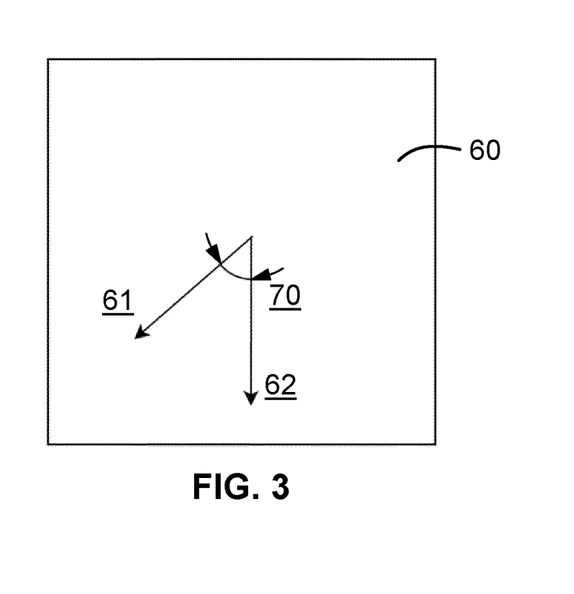
FIG. 3 represents the computation of an orientation difference in accordance with FIGS. 2A and 2B.

FIG. 3 represents the computation of an orientation difference 70 in accordance with FIGS. 2A and 2B.

Figure 4A:
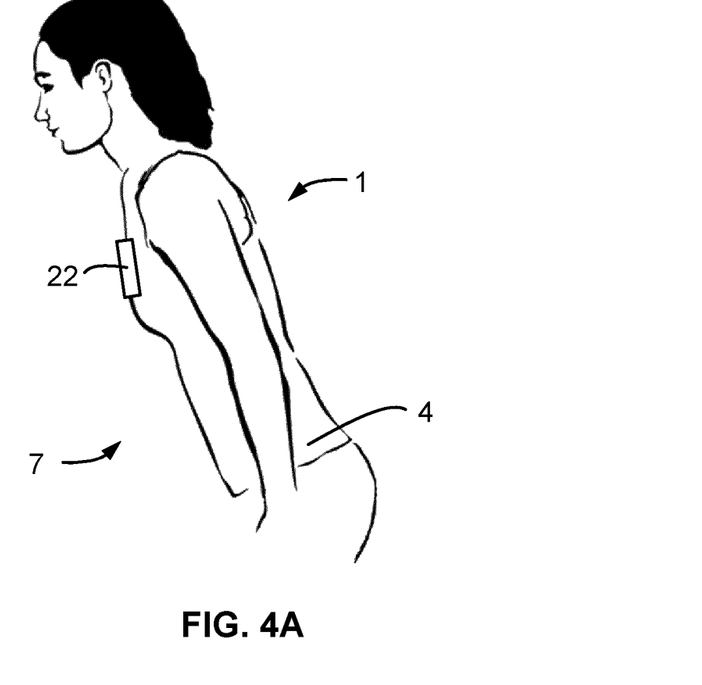
FIGS. 4A and 4B show a person performing variants of a predetermined movement.
Figure 4B:
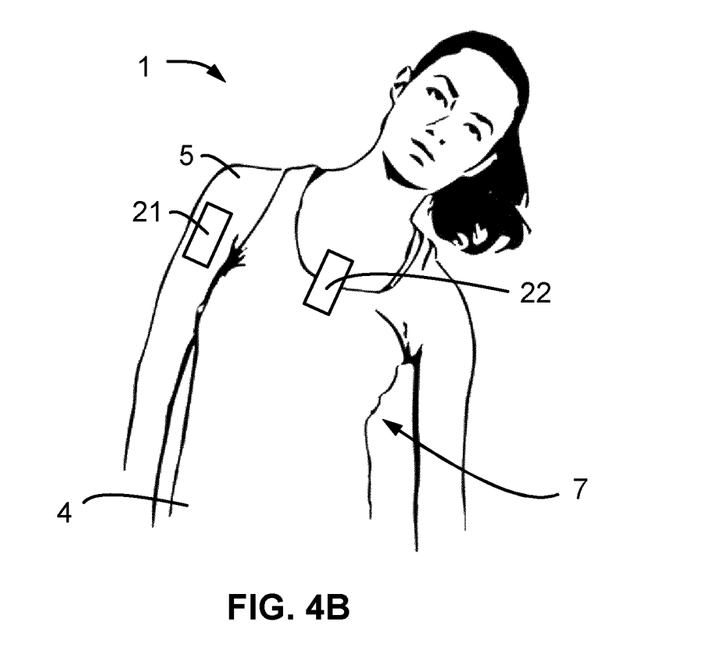

For the computation of the difference, a computing device processes the orientation measurements of the first and second sensors. In particular, the computing device processes, for each sensor, orientation measurements corresponding to two time instants: a first time instant being when the person is standing still as in FIGS. 2A and 2B and, thus, has not started to perform or is about to perform a predetermined movement, and a second time instant being when the person has finished performing the predetermined movement, for example as illustrated in FIGS. 4A and 4B. To this end, in some embodiments, the motion tracking system comprises presenting means (e.g. a screen and/or audio output means) whereby the system requests the person to keep an upright position before performing the predetermined movement.

The computing device at least processes both orientation measurements for each sensor so as to compute the angular displacement for each sensor. The angular displacement corresponds to the angle variation between the orientation measurement at the first time instant and the orientation measurement at the second time instant, that is to say, between the orientation measurement at the first position and the orientation measurement at the second position.

For each angular displacement, the computing device computes the axes of rotation with respect to the local coordinates of the respective sensor as known in the art. Accordingly, the computing device obtains first axes of rotation for the angular displacement corresponding to the first sensor, and second axes of rotation for the angular displacement corresponding to the second sensor.

By way of example, for illustrative purposes only the first axes of rotation are represented by a first vector 61 corresponding to values [0; −0.707; −0.707], whereas the second axes of rotation are represented by a second vector 62 corresponding to [0; −1.00; 0.00]. The first and second vectors 61, 62 are represented on a plane 60 corresponding to the first value of both axes of rotation, which is zero.

The computing device then computes the orientation difference by processing both the first and second axes of rotation as they are indicative of the rotations underwent by the sensors and, thus, the measured orientation rotations. In this example, the orientation difference is represented by an angle 70, which is 45.0°. The computing device then uses this value to adjust the operation of the motion tracking system.

In some embodiments, when the computing device adjusts the operation of the motion tracking system based on the computed orientation difference, it does so by taking into account the orientation difference expected according to the predetermined sensor arrangement. For instance, if the predetermined sensor arrangement establishes that the sensor on the upper arm should be arranged with an orientation difference of 30° with respect to the orientation of the sensor arranged on the chest, if the computed orientation difference were the same of the example above, the computing device would adjust the operation of the motion tracking system based on a value of 45.0° plus 30° or 45.0° minus 30° owing to the expected orientation difference; the expected orientation difference is added or subtracted based on both the orientations with which the sensors are to be arranged on the person (in accordance with the predetermined sensor arrangement) and the orientations of the first and second axes of rotation.

FIGS. 4A and 4B show a person 1 performing variants of a predetermined movement while wearing first and second sensors 21, 22 on a right upper arm 3 and a chest 2 thereof. In both figures, the person 1 tilts the posture by moving a torso 7 thereof with respect to a hip 4 of the person 1.

In the variant of FIG. 4A, the person 1 moves both the torso 7 and the arms forward with respect to the hip 4 so that the first and second sensors 21, 22 both move in the same manner; the arms are adjacent and parallel to the torso 7.

In the variant of FIG. 4B, the person 1 moves the torso 7 and the right arm towards a side, particularly the left side of the person 1, with respect to the hip 4. During the movement, the right arm is kept parallel to the torso 7.

In both variants, the right arm is not rotated with respect to a shoulder 5 connecting the upper arm having the first sensor 21 arranged thereon with the torso 7. In some cases, in both variants the right arm is pressed against a side of the torso 7 so as to avoid inadvertent rotations of the right arm with respect to the shoulder 5 and/or inadvertent movements of the right arm that change the orientation of the sensor arranged thereon with respect to the orientation of the torso 7.

Even though the two variants illustrated correspond to a predetermined movement in which both the arm having the sensor 21 arranged on the upper arm 3 thereof and the torso 7 are moved forward or towards the left side with respect to the hip 4, it is readily apparent that the predetermined movement may involve moving both the arm having the sensor 21 arranged on the upper arm 3 thereof and the torso backward or towards the right side with respect to the hip 4.

In some embodiments, the motion tracking system is configured to require the person 1 to perform a particular variant of the predetermined movement, e.g. both the arm having the sensor 21 arranged on the upper arm 3 thereof and the torso 7 are to be moved forward, or backward, or towards one side with respect to the hip 4. In some other embodiments, the motion tracking system is configured to determine how the person 1 has performed the predetermined movement, i.e. the system determines in which direction both the arm having the sensor 21 arranged on the upper arm 3 thereof and the torso 7 have moved with respect to the hip 4. In this respect, in some embodiments, the motion tracking system comprises presenting means (e.g. a screen and/or audio output means) whereby the system indicates in which direction the person has to perform the predetermined movement, or whether the person can perform the predetermined movement in any direction she/he desires. Also, in some embodiments, the presenting means provide instructions or guidance for performing the predetermined movement.

Figure 5:
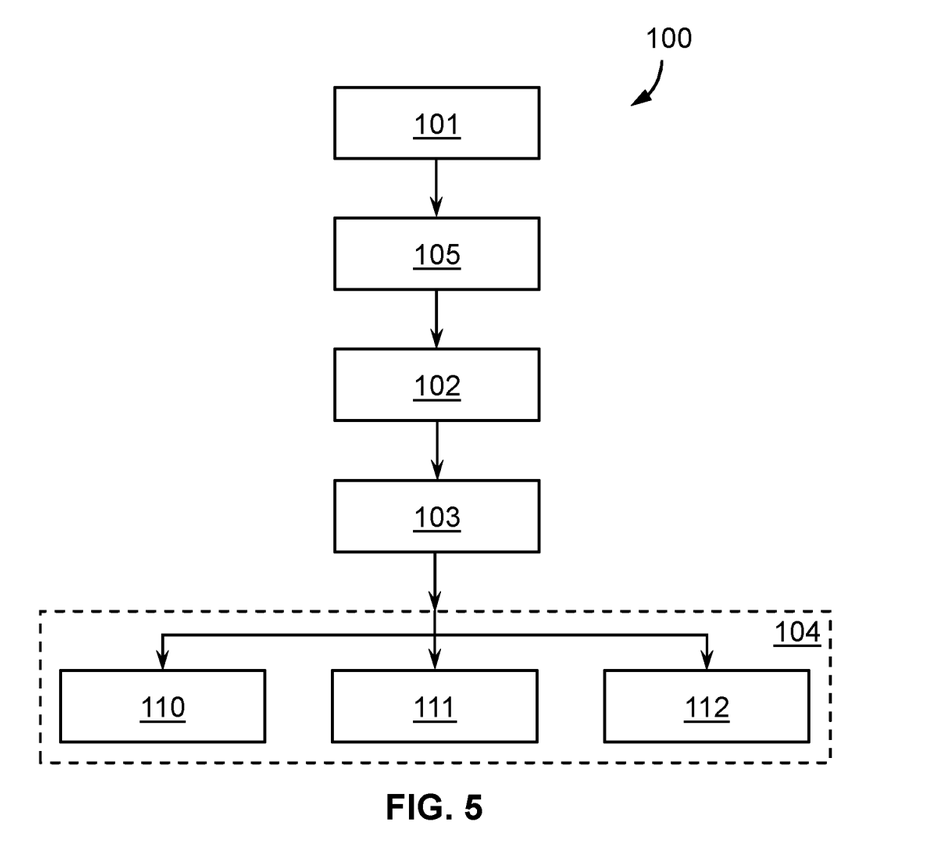
FIG. 5 diagrammatically shows a method in accordance with an embodiment.

FIG. 5 diagrammatically shows a method 100 in accordance with an embodiment.

The method 100 comprises a step of arranging 101 a first sensor of a motion tracking system on an upper arm of a person, and a second sensor of the motion tracking system on a chest of the person; both the first and second sensors at least comprise a gyroscope so that the sensors are capable of measuring orientations.

The first sensor and the second sensor are arranged on the upper arm and the chest, respectively, in accordance with a predetermined sensor arrangement registered in a computing device of the motion tracking system, thus the predetermined sensor arrangement indicating a correspondence between sensors and body members of the person is stored in the computing device (in a memory thereof) before effecting the motion tracking procedure.

The method 100 preferably further comprises a step of calibrating 105 the second sensor. The second sensor preferably comprises an accelerometer for carrying out said calibration. In some embodiments, this calibration 105 step takes place before the arrangement 101 step.

The method 100 further comprises a step in which each of the first and second sensors measure 102 orientations. The orientations are measured while the person with the sensors arranged thereon performs a predetermined movement as described with reference to FIGS. 4A and 4B.

The method 100 further comprises a step in which the computing device digitally processes 103 the orientations measured 102 so as to digitally compute an orientation difference between the orientations measured by the first sensor and the orientations measured by the second sensor.

The method 100 further comprises a step in which the computing device adjusts 104 the operation of the motion tracking system based on the orientation difference computed. The operation can be adjusted in a number of ways 110-112. For instance, the orientations measured by the first sensor or the second sensor can be digitally modified 110 by the computing device so as to compensate for the orientation difference computed, e.g. by applying a quaternion to the orientation measurements of one of the sensors.

Alternatively, a physical exercise evaluation procedure may be digitally adjusted 111 so that the movement sequence provided by the motion tracking system is checked with respect to an adjusted physical exercise evaluation procedure.

The physical exercise evaluation procedure to be digitally adjusted 111 is, for example but not limited to, the evaluation procedure of patent document EP18398006, which is a method for determining a correct reproduction of a movement of a target based on a plurality of orientations thereof at different time instants, the different time instants at least including first and second time instants, the second time instant being posterior to the first time instant, the movement being defined by at least a first predetermined constraint, the first predetermined constraint being defined for first and second orientations of the plurality of orientations and defined by a start angle, an end angle and a first plane definition. In the physical exercise evaluation procedure first and second planes are provided, each defined by the first plane definition, corresponding to the first and second time instants, respectively; a first pair of vectors is provided by projecting the first orientation and the second orientation, corresponding to the first time instant, onto the first plane; a second pair of vectors is provided by projecting the first orientation and the second orientation, corresponding to the second time instant, onto the second plane; first and second angles between the pair of vectors of the first and second pairs of vectors, respectively, are computed; and the correct reproduction of the movement is determined if the first angle is equal to or less than the start angle, and the second angle is equal to or greater than the end angle. The movement is sometimes defined by further predetermined constraints (e.g. second, third, fourth or more predetermined constraints), each defined for two orientations and defined by a start angle, an end angle, and a plane definition, and in order to determine the correct reproduction of the movement the different predetermined constraints shall be met by the tracked target. The adjustment 111 of the physical exercise evaluation procedure entails disregarding or removing one, some or all of these further predetermined constraints from the procedure so as to reduce the number of predetermined constraints to be met for determining the correct reproduction of the movement.

The operation may also be adjusted by providing 112 at least one user perceptible signal indicative of an incorrect placement of the first sensor on the upper arm, and/or at least one user perceptible signal indicative of an instruction to rearrange the first sensor on the upper arm. The motion tracking procedure is preferably paused or stopped and resumed or reinitiated when, upon carrying out the method 100 once again, the orientation difference subsequently computed has a smaller value.

Even though the terms first, second, etc. have been used herein to describe several parameters, variables or devices, it will be understood that the parameters, variables or devices should not be limited by these terms since the terms are only used to distinguish one parameter, variable or device from another. For example, the first sensor could as well be named second sensor, and the second sensor could be named first sensor without departing from the scope of this disclosure.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method for adjusting operation of a motion tracking system at least comprising first and second sensors and a computing device, each of the first and second sensors at least comprising a gyroscope, the method comprising:
    arranging the first sensor on an upper arm of a person, and the second sensor on a chest of the person;
    measuring orientations each of the first and second sensors while the person performs a predetermined movement;
    digitally processing, by the computing device, the orientations measured so as to digitally compute an orientation difference between the orientations measured by the first sensor and the orientations measured by the second sensor; and adjusting, by the computing device, the operation of the motion tracking system based on the orientation difference computed;

wherein the predetermined movement comprises the person moving a torso thereof with respect to a hip of the person, and during the predetermined movement the upper arm is not rotated with respect to a shoulder of the person connected to the upper arm.

2. The method of claim 1, wherein the adjusting of the operation of the motion tracking system comprises one of:
digitally modifying orientations measured by the first sensor or the second sensor;
digitally adjusting a physical exercise evaluation procedure; and
providing at least one of: at least one user perceptible signal indicative of an incorrect placement of the first sensor on the upper arm and at least one user perceptible signal indicative of an instruction to rearrange the first sensor on the upper arm.

3. The method of claim 2, wherein digitally adjusting the physical exercise evaluation procedure comprises digitally adjusting an algorithm with which the motion tracking system digitally determines whether the person tracked with the first and second sensors performs a physical exercise.

4. The method of claim 1, wherein the digitally processing the orientations measured comprises digitally computing the following:
an angular displacement of each of the first and second sensors between a first position in which the person is standing still and a second position in which the person has performed the predetermined movement;
axes of rotation of each of the first and second sensors relative to local coordinates of each of the first and second sensors, respectively, based on the respective angular displacements; and
the orientation difference by digitally computing an angle between the axes of rotation of the first sensor and the axes of rotation of the second sensor.

5. The method of claim 1, further comprising calibrating the second sensor prior to the measuring of the orientations while the person performs the predetermined movement, and wherein the second sensor further comprises an accelerometer.

6. The method of claim 1, wherein each of the first and second sensors further comprises a magnetometer, and wherein in the measuring of the orientations while the person performs the predetermined movement each of the first and second sensors does not process measurements of the magnetometers in respective sensor fusion algorithms thereof.

7. The method of claim 1, wherein the computing device digitally processes the orientations measured to digitally compute the orientation difference irrespective of a direction in which the person has performed the predetermined movement.

8. A motion tracking system comprising:
a computing device comprising at least one processor and at least one memory; and
first and second sensors, each sensor at least comprising a gyroscope;
the at least one processor is configured, together with the at least one memory, to:
digitally process orientations measured by the first and second sensors while a person having the first and second sensors arranged on an upper arm and a chest thereof, respectively, performs a predetermined movement, the orientations being processed so as to digitally compute an orientation difference between the orientations measured by the first sensor and the orientations measured by the second sensor; and
adjust operation of the motion tracking system based on the orientation difference computed;

wherein the predetermined movement comprises the person moving a torso thereof with respect to a hip of the person, and during the predetermined movement the upper arm is not rotated with respect to a shoulder of the person connected to the upper arm.

9. The motion tracking system of claim 8, wherein the at least one processor is configured to adjust the operation of the motion tracking system by one of:
digitally modifying orientations measured by the first sensor or the second sensor;
digitally adjusting a physical exercise evaluation procedure; and
commanding means for providing user perceptible signals to provide at least one of: at least one user perceptible signal indicative of an incorrect placement of the first sensor on the upper arm and at least one user perceptible signal indicative of an instruction to rearrange the first sensor on the upper arm.

10. The motion tracking system of claim 9, wherein the at least one processor is configured to digitally adjust the physical exercise evaluation procedure by digitally adjusting an algorithm with which the motion tracking system digitally determines whether the person tracked with the first and second sensors performs a physical exercise.

11. The motion tracking system of claim 8, wherein the at least one processor is configured to digitally process the orientations measured by digitally computing the following:
an angular displacement of each of the first and second sensors between a first position in which the person is standing still and a second position in which the person has performed the predetermined movement;
axes of rotation of each of the first and second sensors relative to local coordinates of each of the first and second sensors, respectively, based on the respective angular displacements; and
the orientation difference by digitally computing an angle between the axes of rotation of the first sensor and the axes of rotation of the second sensor.

12. The motion tracking system of claim 8, wherein the second sensor further comprises an accelerometer, and wherein the at least one processor is further configured to at least one of calibrate the second sensor and command the second sensor to start a calibration procedure.

13. The motion tracking system of claim 8, wherein each of the first and second sensors further comprises a magnetometer, and wherein each of the first and second sensors is configured to not process measurements of the magnetometers in respective sensor fusion algorithms thereof at least when measuring the orientations while the person performs the predetermined movement.

14. The motion tracking system of claim 8, wherein the at least one processor is configured to digitally process the orientations measured so as to digitally compute the orientation difference irrespective of a direction in which the person has performed the predetermined movement.

15. A computer-readable storage medium comprising instructions which, when executed by a computing device, cause the computing device to perform operations comprising:
digitally processing orientations measured by first and second sensors of a motion tracking system while a person having the first and second sensors arranged on an upper arm and a chest thereof, respectively, performs a predetermined movement, the orientations being processed so as to digitally compute an orientation difference between the orientations measured by the first sensor and the orientations measured by the second sensor, the first and second sensors each comprising a gyroscope; and adjusting operation of the motion tracking system based on the orientation difference computed;

wherein the predetermined movement comprises the person moving a torso thereof with respect to a hip of the person, and during the predetermined movement the upper arm is not rotated with respect to a shoulder of the person connected to the upper arm.

16. The computer-readable storage medium of claim 15, wherein the instructions cause the computing device to adjust the operation of the motion tracking system by one of:

digitally modifying orientations measured by the first sensor or the second sensor;

digitally adjusting a physical exercise evaluation procedure; and providing at least one of: at least one user perceptible signal indicative of an incorrect placement of the first sensor on the upper arm and at least one user perceptible signal indicative of an instruction to rearrange the first sensor on the upper arm.

17. The computer-readable storage medium of claim 16, wherein the instructions cause the computing device to adjust the operation of the motion tracking system by digitally adjusting the physical exercise evaluation procedure, and wherein the adjustment of the physical exercise evaluation procedure comprises digitally adjusting an algorithm with which the motion tracking system digitally determines whether the person tracked with the first and second sensors performs a physical exercise.

18. The computer-readable storage medium of claim 15, wherein the instructions cause the computing device to digitally process the orientations measured by digitally computing the following:

an angular displacement of each of the first and second sensors between a first position in which the person is standing still and a second position in which the person has performed the predetermined movement;

axes of rotation of each of the first and second sensors relative to local coordinates of each of the first and second sensors, respectively, based on the respective angular displacements; and the orientation difference by digitally computing an angle between the axes of rotation of the first sensor and the axes of rotation of the second sensor.

19. The computer-readable storage medium of claim 15, wherein the instructions cause the computing device to digitally process the orientations measured so as to digitally compute the orientation difference irrespective of a direction in which the person has performed the predetermined movement.

20. The computer-readable storage medium of claim 15, wherein each of the first and second sensors further comprises a magnetometer, and wherein the instructions cause the computing device to command each of the first and second sensors not to process measurements of the magnetometers in respective sensor fusion algorithms thereof at least when measuring the orientations while the person performs the predetermined movement.

* * * * *